(12) United States Patent
Eckardt et al.

(10) Patent No.: US 7,002,683 B2
(45) Date of Patent: Feb. 21, 2006

(54) MEASURING HEAD FOR IN LINE DETERMINATION OF THE SIZE OF MOVING PARTICLES IN TRANSPARENT MEDIA

(75) Inventors: Günter Eckardt, Chemnitz (DE); Stefan Dietrich, Chemnitz (DE); Michael Köhler, Oberlungwitz (DE)

(73) Assignee: Parsum-Gesellschaft für Partikel-Strömungs-und Umweltmesstechnik mbH, Chemnitz (DE)

( * ) Notice: Subject to any disclaimer, the term of this patent is extended or adjusted under 35 U.S.C. 154(b) by 72 days.

(21) Appl. No.: 10/469,457

(22) PCT Filed: Feb. 27, 2002

(86) PCT No.: PCT/DE02/00784

§ 371 (c)(1),
(2), (4) Date: Aug. 29, 2003

(87) PCT Pub. No.: WO02/071034

PCT Pub. Date: Sep. 12, 2002

(65) Prior Publication Data

US 2004/0095577 A1   May 20, 2004

(30) Foreign Application Priority Data

Mar. 2, 2001   (DE) ............................... 101 10 066

(51) Int. Cl.
*G01N 15/02* (2006.01)

(52) U.S. Cl. ..................................... 356/336
(58) Field of Classification Search ............ 356/39–43, 356/335–340, 436–440; 422/82.05–82.11; 436/164–165

See application file for complete search history.

(56) References Cited

U.S. PATENT DOCUMENTS

| 5,237,865 A | * | 8/1993 | Wada ........................... 73/198 |
| 6,710,879 B1 | * | 3/2004 | Hansen et al. .............. 356/436 |
| 6,784,981 B1 | * | 8/2004 | Roche et al. ................. 356/39 |

FOREIGN PATENT DOCUMENTS

| DE | 37 14 755  | 11/1995 |
| DE | 44 40 417  | 5/1996  |
| DE | 196 28 348 | 9/1997  |
| DE | 298 04 156 | 7/1998  |

(Continued)

OTHER PUBLICATIONS

Black et al., 1996, "Laser-Based Techniques for Particle-Size Measurement: A Review of Sizing Methods and Their Industrial Applications", *Prog. Energy Combust. Sci.* 22:267-306.

*Primary Examiner*—Tu T. Nguyen
(74) *Attorney, Agent, or Firm*—Collard & Roe, P.C.

(57) ABSTRACT

A measuring head for determining particle size in transparent media, comprising a measuring head body which has an opening for an optical measuring point with two measuring windows, consisting of an illuminating device and a light receiving device which is connected to an opto-electronic converter device. A rinsing device is used to clean the optical measuring point. The windows can be reliably prevented from becoming fouled or wetted by particles contained in the particle flow, enabling optical permeability of the measuring point and avoiding false measuring values. The rinsing device has a rinsing medium source, a channel extending to the opening inside the measuring head body for delivery of a rinsing medium and at least one discharge opening near the opening, which extends perpendicularly to and directly in front of the measuring windows. At least one defined rinsing jet is spread over the surfaces of the measuring windows.

9 Claims, 3 Drawing Sheets

FOREIGN PATENT DOCUMENTS

| | | |
|---|---|---|
| DE | 298 23 184 | 4/1999 |
| DE | 199 11 654 | 12/2000 |
| GB | 2274332 | 7/1994 |
| WO | WO 87 05108 | 8/1987 |

* cited by examiner

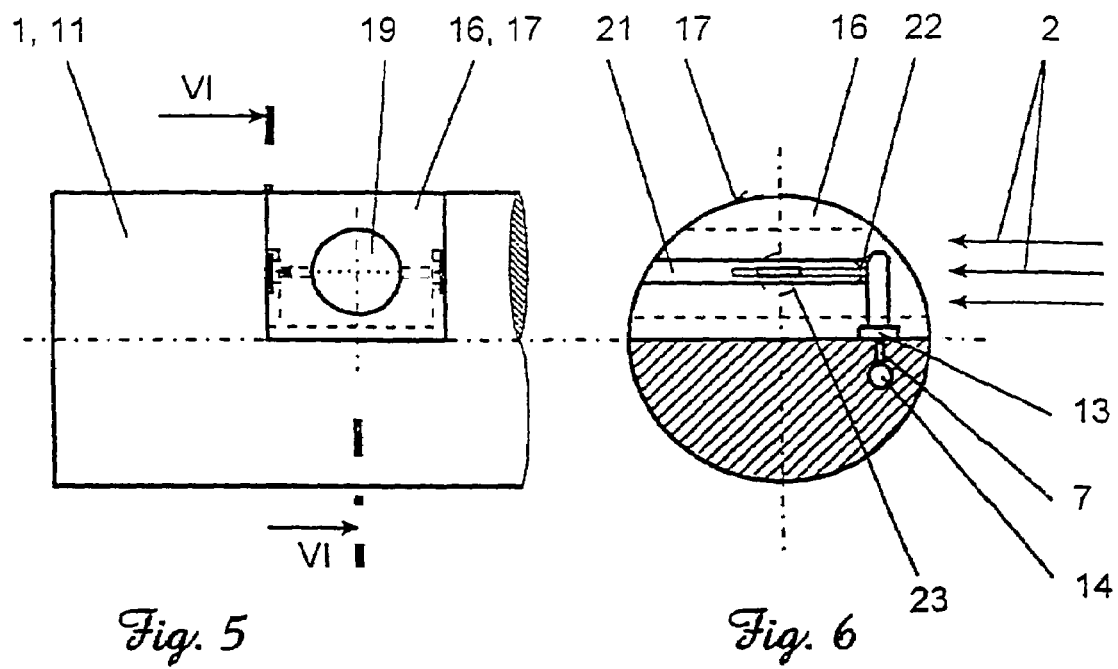

MEASURING HEAD FOR IN LINE DETERMINATION OF THE SIZE OF MOVING PARTICLES IN TRANSPARENT MEDIA

CROSS REFERENCE TO RELATED APPLICATIONS

Applicants claim priority under 35 U.S.C. §119 of GERMAN Application No. 101 10 066.3 filed on Mar. 2, 2001. Applicants also claim priority under 35 U.S.C. §365 of PCT/DE02/00784 filed on Feb. 27, 2002. The international application under PCT article 21(2) was not published in English.

BACKGROUND OF THE INVENTION

1. Field of the Invention

The invention relates to a measuring head for in-line determination of the size of moving particles in transparent media, comprising a tube-shaped measuring head body which has a parallel-walled opening, open on one side, in the region of its front end, located in the measuring space, for holding an optical measuring point with two measuring windows, consisting of an illuminating device arranged in an opening wall and a light receiving device provided in the opposite opening wall, which is connected to an optoelectronic converter device, whereby the particle flow is located between the illuminating device and the light receiving device, with the use of a rinsing device for cleaning the optical measuring point, whereby the rinsing device consists of a rinsing medium source, a channel leading as far as the opening inside the tube-shaped measuring head body for delivery of the rinsing medium, and at least one discharge opening in the region of the opening.

2. The Prior Art

The area of application of the invention is contact-free determination of the size of particles, i.e. solid, liquid and/or gaseous particles that are located in flowing fluids or gases or that are moving in a transparent medium or in a vacuum itself. Examples are dispersed multi-phase flows, e.g. dust flows, suspension flows, or aerosol flows, whereby the particle size can be determined without sampling, at a high data rate, in technological processes of lesser or greater complexity.

According to DE 196 28 348 C1 and DE 298 04 156 U1, such a measuring head is already known. It consists of a tube-shaped measuring head body, which can be introduced into a medium that carries particles. At the end of the measuring head body, there is a parallel-walled opening that is open on one side, and which has an optical measuring point assigned to it. The latter has two measuring windows located opposite one another in the opening, whereby one measuring window protects an illuminating device, and the other measuring window protects a spatial-frequency filter arrangement as a light receiving arrangement, with an additional light-wave guiding element. This spatial-frequency filter arrangement is passed to an opto-electronic converter device on the output side, so that when particles pass through the measuring volume illuminated by the illuminating device, in the opening of the measuring head body, an output signal of an alternating voltage type can be evaluated to determine the particle velocity on the one hand, and an impulse signal can be evaluated to determine the particle size, on the other hand.

An analog measuring head with a different light receiving arrangement, which obtains the output signals on the basis of time measurements, is known from DE 199 11 654 C1.

In the practical use of these known measuring heads in different particle flows, it has been shown that relatively rapid wetting or fouling of the two measuring windows of the optical measuring point takes place, particularly in the presence of dusty and/or sticky particles. The measuring windows close up as a result of the deposit of such particles, so that the optical permeability of the measuring point deteriorates to an increasing degree. As a result, exact output signals can no longer be determined, i.e. undesirable measuring errors occur in the determination of the particle size.

It is true that it is already known, from DE 298 23 184 U1, to equip an optical measuring head for determining the velocity of flowing fluids with a rinsing device for cleaning the optical measuring point. In this connection, the goal is to prevent floating materials entrained by the flow, particularly light materials, with a more or less bulky shape, such as grass blades, leaves, etc., from getting stuck in an intake channel of a plate-shaped head body that contains the optical measuring point, i.e. to prevent damage to a knife-like edge of the intake channel, if necessary. In this connection, this rinsing device consists of a line that conducts a pressure medium, which opens out centered in the back opening region of the intake channel of the plate-shaped head body, i.e. seen in the flow direction, after the optical measuring point assigned to the intake channel, and opposite to the incoming flow direction.

This known rinsing device is not suitable for use in the measuring head for determining particle size according to the general type, since cleaning and constantly keeping the two measuring windows of the optical measuring point clear, particularly of deposited (correspondingly small) particles of the particle flow is not provided and also not possible. The rinsing jet, which is directed against the inflow direction, is weakened at the higher flow velocities of the particle flow that is usual in technical processes, in such a way that an effective cleaning effect in the stated sense cannot be achieved at the two measuring windows. Also, the relatively, large distance of the outflow opening of the rinsing device from the measuring windows has a negative effect on the cleaning effect. Furthermore, the known arrangement of the rinsing device causes a disturbance of the particle flow in the region of the optical measuring point, and this results in inaccurate measurement results with regard to the particle velocity.

Furthermore, a measuring device for determining the powder portion in a gas/powder stream is known from DE 44 40 417 A1, which can be used in a transport line that carries the said gas/powder stream. It consists of a light-permeable housing for the gas/powder stream, through which the beams of a beam transmitter to a beam receiver pass. An insert pipe for carrying the gas/powder stream is arranged within the housing. This pipe has passage openings in the region of the beam path. A pure gas stream that flows in the annular gap between the insert pipe and the housing is supposed to prevent deposits on the inside wall of the housing and on light guides.

This known device is relatively complicated and therefore expensive, particularly because of the provision of a pure gas flow that completely surrounds the gas/powder stream. Furthermore, the described measures for preventing deposits on a measuring head for determining particle size according to the general type cannot be used, since here the particle flow is not carried in a closed housing (of the measuring device). Accordingly, the arrangement of an annular gap for carrying a pure gas stream cannot be implemented. Furthermore, the gas stream that flows in the annular gap cannot prevent the deposition of deposits in the interior of the insertion pipe of the passage openings, so that incorrect measurement values cannot be precluded.

Furthermore, a measuring head of the general type is known from WO 87/05 108 A1. Here, the rinsing device assigned to the illuminating device and the light receiving device, for cleaning the optical measuring point, essentially consists of channels that run parallel to the surfaces of the lenses, in each instance, for delivery of the rinsing medium, which channels empty into bores for guiding the light beam, arranged perpendicular to the particle flow.

However, this known arrangement is connected with disadvantages in terms of flow technology and function.

SUMMARY OF THE INVENTION

In view of the disadvantages of the known state of the art, the invention is based on the task of creating a measuring head for determining particle size, of the type stated initially, where the measuring windows of the optical measuring point are reliably freed of fouling or wetting by particles of the particle stream and constantly kept clear, so that the optical permeability of the measuring point is assured over a long useful lifetime and particle deposit or wetting is avoided, to the greatest extent.

This task is accomplished, according to the invention, by means of a rinsing insert that can be inserted into, attached in, and replaced in the parallel-walled opening, which insert partially or completely supplements the cross-section of the tube-shaped measuring head body in the region of the opening, seen in axial cross-section, which insert furthermore possesses an inlet opening connected with the source of a rinsing medium by way of the channel and with the discharge opening that opens perpendicular to the measuring windows of the optical measuring point, and two discharge openings for the rinsing medium connected with the inlet opening, which discharge openings run perpendicular to the measuring windows of the illuminating device and the light receiving arrangement, in each instance.

In this measuring head, structured according to the invention, the two measuring windows of the optical measuring point are constantly and reliably protected against fouling and wetting caused by the deposit of particles of the particle flow, since the rinsing device arranged and formed in the opening for this purpose guarantees the constant application of at least one thin rinsing jet of sufficient jet strength directly tangentially oriented over the surfaces of the two measuring windows ("mantle flow" in the direction of the particle flow). Accordingly, even the formation of deposits on the measuring windows is prevented. On the other hand, any fouling or deposits already formed due to non-activation of the rinsing device, for example, is reliably removed by means of the rinsing jet, directed accordingly. In this way, the optical permeability of the measuring point is assured over long periods of use, even in the case of problematic particle flows (e.g. particularly dusty or sticky products), so that incorrect measurement values as well as separation effects caused by fouling or particle deposit are avoided, to the greatest possible extent. This is of particular importance in the case of automatic long-term use of the measuring head.

The use, according to the invention, of a rinsing insert that can be inserted into the opening of the tube-shaped measuring head body and replaced allows universal use of the measuring body as well as a further improvement of the cleaning effect in the region of the two measuring windows of the optical measuring point. The rinsing jet, in particular, can be precisely pre-selected and defined with regard to its jet direction and intensity relative to the particle flight path, so that optimal results can be achieved. Because of the easy exchangeability of the rinsing insert, it can be cleaned, when required, without much assembly or other work.

It is practical, particularly for use in particle flows with larger particles, that the rinsing insert, which partially supplements the cross-section of the tube-shaped measuring head body in the region of the opening, has an inside delimitation surface that contains the inlet opening, which surface rests against the inside surface of the parallel-walled opening, and an outside delimitation surface that runs parallel to the former, whose center-to-center distance from the longitudinal axis of the tube-shaped measuring body is less than the center-to-center distance of the light receiving arrangement, and whereby a discharge channel for the rinsing medium, connected with the inlet opening, is arranged in both face walls of the rinsing insert, with the discharge opening defining a jet direction of the rinsing jet, in each instance, which direction encloses an acute angle to the direction of the particle flow.

In this connection, it is practical if the outside delimitation surface of the rinsing insert, which runs parallel, is profiled in groove shape, for example, parallel to the particle flow, in order to achieve a more advantageous orientation of the particle flight path.

It is advantageous, particularly for use in particle flows with smaller particles, that the rinsing insert, which completely supplements the cross-section of the tube-shaped measuring head body in the region of the opening, has an inside delimitation surface that contains the inlet opening, which surface rests against the inside surface of the parallel-walled opening, and an outside delimitation surface that supplements the cross-section, whereby the rinsing insert possesses a particle guide channel that passes through it, runs parallel to the inside delimitation surface and aligned flush and perpendicular with the direction of effect of the measuring windows of the illuminating device and the light receiving device, which channel has openings that penetrate the rinsing insert, assigned to the measuring windows in the region of the windows, in each instance, and whereby a discharge channel for the rinsing medium, connected with the inlet opening, is arranged in both face walls of the rinse insert, which channel runs parallel to the particle guide channel and leads past the measuring windows in perpendicular manner.

In this connection, it is particularly advantageous if throttle jets are provided in the discharge channels for the rinsing medium, whose narrowings in cross-section, seen in the direction of the flow of the rinsing medium, are arranged in front of the measuring windows, in each instance. These throttle jets act like an injector, i.e. the particle flow is accelerated in the region of the measuring windows, so that better measurement results can be achieved, particularly by means of separating the particles of a particle flow of greater particle density. On the other hand, the jet-related increase in the flow velocity of the rinsing medium makes it possible to achieve a further improvement in the cleaning effect.

It is practical if the source of the rinsing medium generates a suitable excess pressure of the rinsing medium relative to the pressure of the medium that carries the particles, in order to achieve an effective rinsing jet.

It is furthermore practical that the rinsing medium consists of a compressed gas, of a compressed liquid, or of a compressed gas mixed with a compressed liquid (or vice versa). The use of compressed air as a rinsing medium is particularly simple and effective.

For the purpose of avoiding a kick-back of the medium that carries the particles and is under pressure, it is advantageous if a kick-back valve is arranged in the channel for feed of the rinsing medium.

BRIEF DESCRIPTION OF THE DRAWINGS

The invention will be explained in greater detail in the following, using several exemplary embodiments. The related drawings show.

Figure 1:
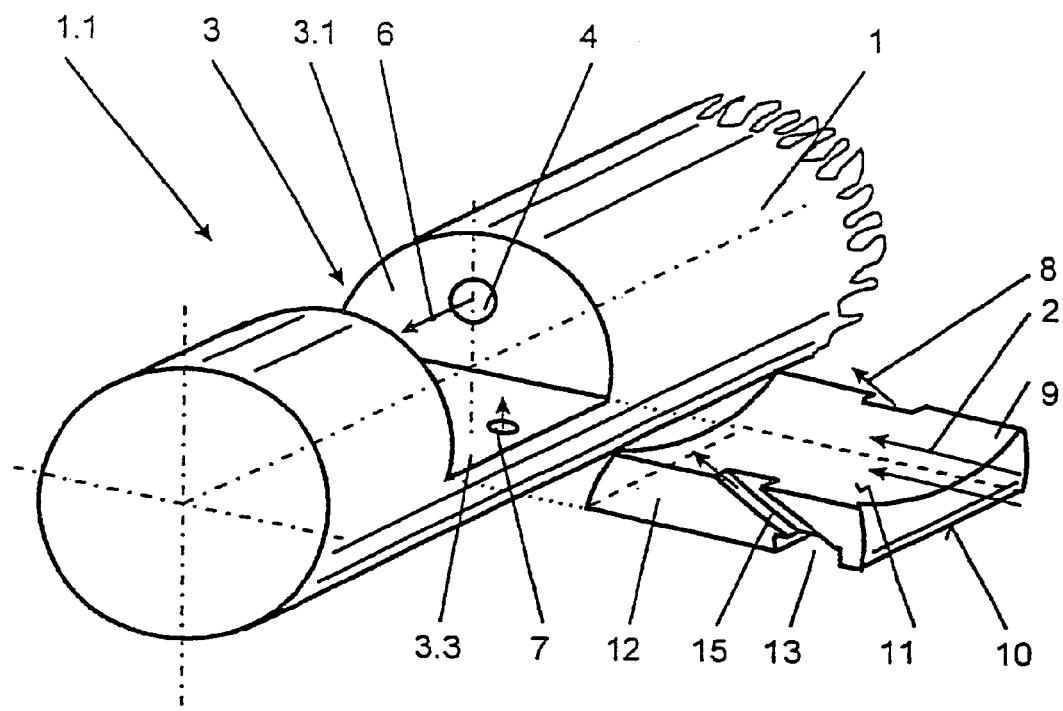
FIG. 1 a perspective view of a first exemplary embodiment with a rinsing insert prepared for insertion, FIG. 2 the side view of FIG. 1, with the rinsing insert inserted, FIG. 3 the cross-section along line III—III in FIG. 2, FIG. 4 a perspective view of a second exemplary embodiment with another rinsing insert prepared for insertion, FIG. 5 the side view of FIG. 4, with the rinsing insert inserted, FIG. 6 the cross-section along line VI—VI in FIG. 5.

The measuring head consists of a housing (not shown) for holding, among other things, a light source, electronic and electrical components, and a source of a rinsing medium. A tube-shaped measuring head body 1 is attached to the housing, the front end 1.1 of which body can project into a measuring space. A particle flow 2 is located in this measuring space, for example in a pipeline, whereby the size of the moving particles is supposed to be determined.

The tube-shaped measuring head body 1 contains a parallel-walled opening 3, open on one side, having two opening walls 3.1 and 3.2, as well as an inside surface 3.3 in the region of the front end 1.1. The opening 3 serves to hold an optical measuring point. The latter has two measuring windows 4, 5 arranged opposite one another, whereby the measuring window 4 is located in the opening wall 3.1 and represents the outlet opening of an illuminating device, which is in connection with the light source (not shown) arranged in the housing. Accordingly, a parallel light beam 6 exits from the measuring window 4 when the light source is activated.

The measuring window 5 located in the opening wall 3.2 protects a spatial-frequency filter arrangement known from DE 196 28 348 C1, having an additional light-wave-guiding element (not shown), which is passed to an opto-electronic converter arrangement on the output side. According to the arrangement, the particles of the particle flow 2 that move through the parallel-walled opening 3 (measuring volume) are illuminated by the light beam 6, whereby corresponding shadow images are imaged on the measuring window 5, i.e. on the optical active surface of the aforementioned spatial-frequency filter arrangement, so that the known signals can be evaluated for determining the particle size.

Figures 2, 3:
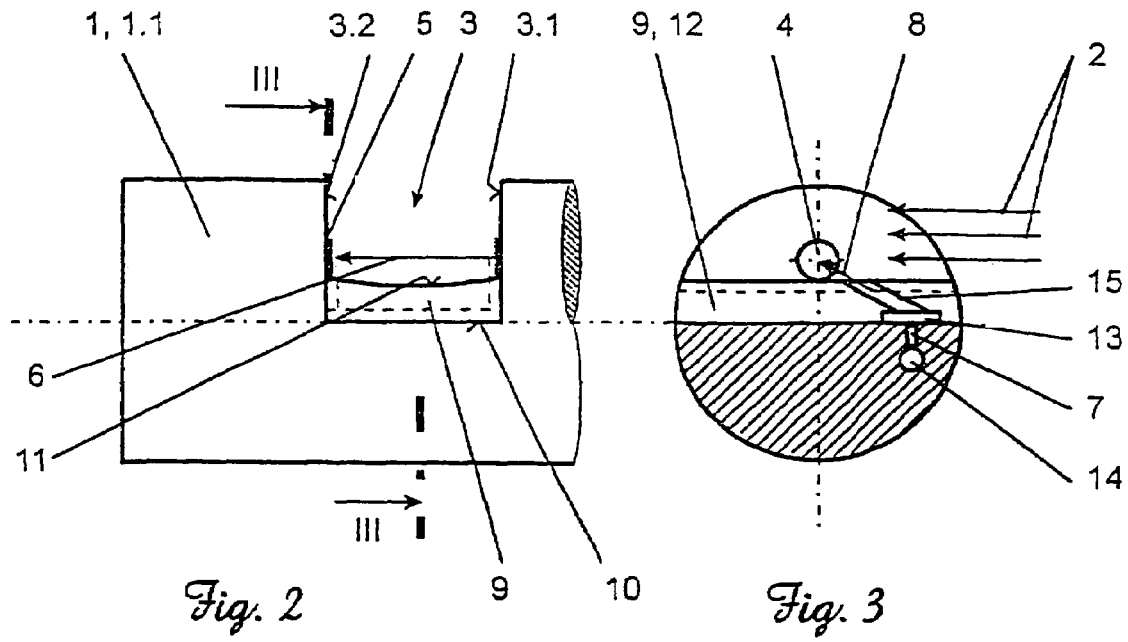

In the first exemplary embodiment of a rinsing device for the measuring windows 4, 5 of the optical measuring point (FIGS. 1–3), the latter consists of the source of a rinsing medium, already mentioned and arranged in the housing, e.g. a compressed air connector (not shown), which is connected, by way of a kick-back valve (to avoid kick-back effects caused by the pressure of the particle flow 2), with a channel 14 that is located in the interior and extends along the tube-shaped measuring head body 1. This channel 14 leads up to the parallel-walled opening 3 and empties out there, into a discharge opening 7, in each instance.

According to the first exemplary embodiment (FIGS. 1–3), the rinsing device has a rinsing insert 9, which can be inserted into the parallel-walled opening 3 and attached in suitable manner, as well as replaced, if necessary. As is particularly evident from FIG. 3, the semicircular cross-section of the tube-shaped measuring head body 1 is partially supplemented by the cross-section of the rinsing insert 9, in the region of the parallel-walled opening 3.

The rinsing insert 9 has an inside delimitation surface 10 that rests against the inside surface 3.3 of the opening 3, as well as an outside delimitation surface 11 that is essentially parallel to the former, and two face walls 12. The outside delimitation surface 11 is profiled parallel to the particle flow 2, for example in groove shape according to a partial cylinder outside surface, in order to achieve an advantageous alignment of the particle flight path relative to the measuring windows 4, 5. The center-to-center distance of the outside delimitation surface 11 from the longitudinal axis of the tube-shaped measuring head body 1 is smaller than the center-to-center distance of the grid axis of the spatial-frequency filter arrangement behind the measuring window 5, so that during the measuring process, the light beam 6 can impact the spatial-frequency arrangement unhindered by the rinsing insert 9.

DETAILED DESCRIPTION OF PREFERRED EMBODIMENTS

A groove 13 (as an inlet opening for the rinsing medium) that runs parallel to the width of the rinsing insert 9, i.e. the opening 3, is arranged in the inside delimitation surface 10 of the rinsing insert 9, and the discharge opening 7 connected with the channel 14 opens into this groove. Furthermore, discharge channels 15 for the rinsing medium are worked into the face walls 12, which end in the groove 13, on the one hand, and in the outer delimitation surface 11 in the region of the measuring windows 4, 5, in each instance, on the other hand. The arrangement of the discharge channels 15 relative to the measuring windows 4, 5 determines a rinsing jet 8, in each instance, the jet direction of which encloses an acute angle relative to the particle flow 2.

When rinsing medium is supplied by way of the channel 14, it enters into the groove 13 of the rinsing insert 9 by way of the discharge opening 7, and from there it exits through the two discharge channels 15, in such a way that correspondingly thin rinsing jets 8 sweep crosswise over the surfaces of the measuring windows 4, 5, in each instance. The acute angle between the jet direction of the rinsing jet 8 and the direction of the particle flow 2 results in an improvement in the cleaning effect of the rinsing jet 8, since the rinsing medium is accelerated by the particle flow 2, in the direction towards the measuring windows 4, 5.

Figure 4:
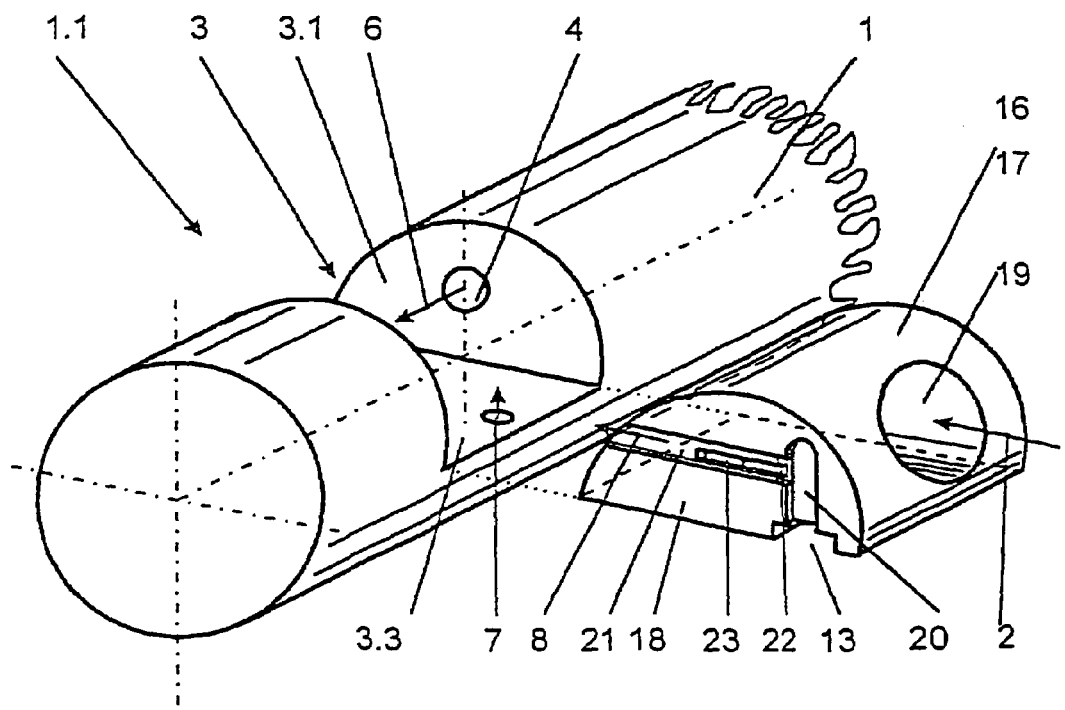

Corresponding to the second exemplary embodiment (FIGS. 4–6), the rinsing device is equipped with a different rinsing insert 16, which, however, can also be inserted, attached and replaced in the parallel-walled opening 3. From FIG. 6, it is evident that the semicircular cross-section of the tube-shaped measuring head body 1 is completely supplemented in the region of the opening 3, i.e. the opening 3 is completely filled by the rinsing insert 16.

The rinsing insert 16 also has an inside delimitation surface 10 that rests against the inside surface 3.3 of the opening 3. The outside delimitation surface 17 of the rinsing insert 16, however, corresponds to the cylindrical mantle surface (which is interrupted in the region of the opening 3) of the tube-shaped measuring head body 1, for the reason indicated above. The two face walls 18 of the rinsing insert 16 are essentially analogous to the opening walls 3.1, 3.2 against which they rest.

The rinsing insert 16 is furthermore penetrated by a particle guide channel 19. This runs parallel to the inside delimitation surface 10, i.e. to the inside surface 3.3 of the parallel-walled opening 3, and perpendicular to the direction of effect of the light beam 6, since the tube-shaped measuring head body 1 is usually aligned in accordance with the direction of the particle flow 2, with regard to the surfaces of its opening 3. Accordingly, the particle flow 2 flows through the rinsing insert 16 by means of the particle guide channel 19.

For the purpose of feeding in the rinsing medium, the rinsing insert 16 also has a groove 13 in its inside delimitation surface 10, into which groove the discharge opening 7 empties. A feed channel 20, which is connected with a discharge channel 21, in each instance, and is worked into each face wall 18, ends in the groove 13, in each instance. These discharge channels 21 run parallel to the particle guide channel 19, past the measuring windows 4, 5, in perpendicular manner, and end in the region of the outlet of the opening 3.

A throttle jet 22 is arranged in each discharge channel 21. The narrowing of the cross-section of this jet is located in front of the measuring windows 4, 5, in each instance, seen in the direction of the flow of the rinsing medium.

To allow the light beam 6 to pass through, an opening 23 that penetrates the rinsing insert 16 in the region of the measuring windows 4, 5, in each instance, is furthermore worked into each discharge channel 21, i.e. on both sides of the particle guide channel 19, which opening preferably possesses the shape of a gap that extends flush to the grid axis of the spatial-frequency filter arrangement.

If, in this embodiment, the rinsing medium is fed in by way of the channel 14 and the discharge opening 7, it slows through both feed channels 20 to the discharge channels 21, by means of the groove 13. Under the effect of the throttle jets 22 arranged there, the flow of the rinsing medium is accelerated, so that a (further) improvement in the cleaning effect can be achieved by means of the rinsing jet 8, with regard to the surfaces of the measuring windows 4, 5. In addition, this arrangement of the throttle jets 22 acts as an injector, in each instance, i.e. the particle flow 2 is accelerated in the particle guide channel 19, in the region of the openings 23, next to the measuring windows 4, 5. As a result, more precise measurement results can be achieved, particularly in the case of particle flows with a greater particle density, by means of an additional dispersion effect.

In the above exemplary embodiments, compressed air, which has a suitable excess pressure relative to the pressure of the particle flow 2, was used as the rinsing medium. In the same manner, and independent of the concrete case of use, a different compressed gas or a compressed liquid can also be used as the rinsing medium. In this connection, the use of the medium of the particle flow 2 as the rinsing medium is obvious. Likewise, the use of compressed gas mixed with compressed liquid (or vice versa) is possible.

The invention is not limited by details of the above exemplary embodiments. In particular, the light receiving arrangement can also be implemented in another suitable way, e.g. according to DE 199 11 654 C1.

REFERENCE SYMBOL LIST 1 measuring head body
1.1 front end
2 particle flow
3 opening
3.1 opening wall
3.2 opening wall
3.3 inside surface
4 measuring window
5 measuring window
6 light beam
7 discharge opening
8 rinsing jet
9 rinsing insert
10 inside delimitation surface
11 outside delimitation surface
12 face wall
13 groove
14 channel
15 discharge channel
16 rinsing insert
17 outside delimitation surface
18 face wall
19 particle guide channel
20 feed channel
21 discharge channel
22 throttle jet
23 opening

The invention claimed is:

1. Measuring head for in-line determination of the size of moving particles in transparent media, comprising a tube-shaped measuring head body which has a parallel-walled opening, open on one side, in the region of its front end, located in the measuring space, for holding an optical measuring point with two measuring windows, the optical measuring point consisting of an illuminating device arranged in an opening wall and a light receiving device provided in the opposite opening wall, the light receiving device is connected to an opto-electronic converter device, whereby the particle flow is located between the illuminating device and the light receiving device, the measuring head includes a rinsing device for cleaning the optical measuring point, whereby the rinsing device consists of a rinsing medium source, a channel leading as far as the opening inside the tube-shaped measuring head body for delivery of the rinsing medium, and discharge openings in the region of the opening, the rinsing device is characterized by a rinsing insert (9; 16) that can be inserted into, attached in, and replaced in the parallel-walled opening (3), the rinsing insert partially or completely supplements the cross-section of the tube-shaped measuring head body (1) in the region or the opening (3), seen in axial cross-section, the rinsing insert furthermore possesses an inlet opening (13) connected with the source of a rinsing medium by way of the channel (14) and with the discharge opening (7) that opens perpendicular to the measuring windows (4; 5) of the optical measuring point, and two discharge openings (15; 21) for the rinsing medium connected with the inlet opening, the discharge openings run perpendicular to the measuring windows (4; 5) of the illuminating device and the light receiving arrangement, respectively.

2. Measuring head according to claim 1, characterized in that the rinsing insert (9), which partially supplements the cross-section of the tube-shaped measuring head body (1) in the region of the opening (3), has an inside delimitation surface (10) that contains the inlet opening (13), the inside delimitation surface rests against the inside surface (3.3) of the parallel-walled opening (3), and an outside delimitation surface (11) that runs parallel to the inside delimitation, the center-to-center distance of the outside delimitation surface from the longitudinal axis of the tube-shaped measuring body (1) is less than the center-to-center distance, of the light receiving arrangement, and whereby a discharge channel (15) for the rinsing medium, connected with the inlet opening (13), is arranged in both face walls (12) of the rinsing insert (9), with the discharge opening defining a jet direction of the rinsing jet (8), in each instance, the direction encloses an acute angle to the direction of the particle flow (2).

3. Measuring head according to claim 2, characterized in that the outside delimitation surface (11) of the rinsing insert (9), which runs parallel to the two face walls, is profiled parallel to the particle flow (2).

4. Measuring head according to claim 1, characterized in that the rinsing insert (16), which completely supplements the cross-section of the tube-shaped measuring head body (1) in the region of the opening (3), has an inside delimitation surface (10) that contains the inlet opening (13), the inside delimitation surface rests against the inside surface (3.3) of the parallel-walled opening (3), and an outside delimitation surface (17) that supplements the cross-section, whereby the rinsing insert (16) possesses a particle guide channel (19) that passes through the rinsing insert, the particle guide channel runs parallel to the inside delimitation surface (10), and is aligned flush and perpendicular with the direction of effect of the measuring windows (4; 5) of the illuminating device and the light receiving device, which channel has openings (23) that penetrate the rinsing insert (16), in the region of the measuring windows (4; 5) in the region of the windows, respectively, and whereby a discharge channel (21) for the rinsing medium, connected with the inlet opening (13), is arranged in both face walls (18) of the rinse insert (16), the discharge channel runs parallel to the particle guide channel (19) and leads past the measuring windows (4; 5) in perpendicular manner.

5. Measuring head according to claim 4, characterized by throttle jets (22) that are provided in the discharge channels (21) for the rinsing medium, the narrowing in cross-section of the jets, seen in the direction of the flow of the rinsing medium, are arranged in front of the measuring windows (4; 5), in each instance.

6. Measuring head according to claim 1, characterized in that the source of the rinsing medium generates a suitable excess pressure of the rinsing medium relative to the pressure of the medium that carries the particles.

7. Measuring head according to claim 1, characterized in that the rinsing medium consists of a compressed gas, of a compressed liquid, or of a compressed gas mixed with a compressed liquid (or vice versa).

8. Measuring head according to claim 7 characterized by the use of compressed air as the rinsing medium.

9. Measuring head according to claim 1, characterized in that a kick-back valve is arranged in the channel (14) for feed of the rinsing medium.

* * * * *